(12) United States Patent
Morgan et al.

(10) Patent No.: US 8,997,578 B2
(45) Date of Patent: Apr. 7, 2015

(54) METHODS FOR DETERMINING REACTIVE INDEX FOR CEMENTITIOUS COMPONENTS, ASSOCIATED COMPOSITIONS, AND METHODS OF USE

(71) Applicant: Halliburton Energy Services, Inc., Houston, TX (US)

(72) Inventors: Ronnie G. Morgan, Waurika, OK (US); D. Chad Brenneis, Marlow, OK (US); Craig W. Roddy, Duncan, OK (US)

(73) Assignee: Halliburton Energy Services, Inc., Houston, TX (US)

( * ) Notice: Subject to any disclaimer, the term of this patent is extended or adjusted under 35 U.S.C. 154(b) by 273 days.

(21) Appl. No.: 13/662,155

(22) Filed: Oct. 26, 2012

(65) Prior Publication Data

US 2014/0116150 A1    May 1, 2014

(51) Int. Cl.
| | |
|---|---|
| G01N 3/00 | (2006.01) |
| C09K 8/46 | (2006.01) |
| G01N 33/38 | (2006.01) |
| E21B 33/13 | (2006.01) |
| C04B 28/04 | (2006.01) |
| C04B 18/16 | (2006.01) |
| C09K 8/42 | (2006.01) |
| C04B 28/02 | (2006.01) |
| C04B 28/14 | (2006.01) |

(52) U.S. Cl.
CPC ............... *C09K 8/46* (2013.01); *G01N 33/388* (2013.01); *E21B 33/13* (2013.01); *C04B 28/04* (2013.01); *C04B 18/162* (2013.01); *C09K 8/428* (2013.01); *C04B 28/021* (2013.01); *C04B 28/14* (2013.01)

(58) Field of Classification Search
CPC ................................ G01N 33/388; C09K 8/50
USPC ...................................... 73/803, 818; 166/293
See application file for complete search history.

(56) References Cited

U.S. PATENT DOCUMENTS

| | | | |
|---|---|---|---|
| 4,967,839 A | 11/1990 | Carpenter et al. | |
| 5,383,521 A | 1/1995 | Onan et al. | |
| 5,454,867 A | 10/1995 | Brothers et al. | |
| 5,571,318 A | 11/1996 | Griffith et al. | |
| 5,968,255 A | 10/1999 | Metha et al. | |
| 7,077,203 B1 | 7/2006 | Roddy et al. | |
| 7,090,721 B2 * | 8/2006 | Craig et al. | 106/35 |
| 7,353,870 B2 | 4/2008 | Roddy et al. | |
| 7,395,860 B2 * | 7/2008 | Roddy et al. | 166/293 |
| 7,442,249 B2 | 10/2008 | Mueller | |
| 7,445,669 B2 | 11/2008 | Roddy et al. | |
| 7,488,762 B2 * | 2/2009 | Takano et al. | 523/117 |
| 7,631,692 B2 | 12/2009 | Roddy et al. | |
| 8,075,687 B2 * | 12/2011 | Testud | 106/789 |

(Continued)

FOREIGN PATENT DOCUMENTS

WO    2007028951 A1    3/2007

OTHER PUBLICATIONS

International Search Report and Written Opinion for Application No. PCT/US2013/066767 dated Dec. 23, 2013.

*Primary Examiner* — Max Noori
(74) *Attorney, Agent, or Firm* — Craig W. Roddy; Tumey L. L. P.

(57) ABSTRACT

A variety of methods and compositions are included, without limitation, a method of cementing includes providing a settable composition comprising water and a cementitious component having a determined reactive index; and allowing the settable composition to set to form a hardened mass.

24 Claims, 4 Drawing Sheets

(56) References Cited

U.S. PATENT DOCUMENTS

| | | |
|---|---|---|
| 8,281,859 B2 | 10/2012 | Roddy et al. |
| 8,609,595 B2 * | 12/2013 | Morgan et al. ............. 507/269 |
| 2008/0087472 A1 | 4/2008 | Fout |
| 2008/0257223 A1 * | 10/2008 | Testud ...................... 106/789 |
| 2009/0298724 A1 | 12/2009 | Getzlaf et al. |
| 2011/0000400 A1 | 1/2011 | Roddy |
| 2012/0160131 A1 | 6/2012 | Roddy |
| 2012/0227631 A1 | 9/2012 | Roddy et al. |
| 2012/0234541 A1 | 9/2012 | Roddy et al. |
| 2013/0048286 A1 | 2/2013 | Morgan et al. |
| 2014/0048266 A1 * | 2/2014 | Morgan et al. ............. 166/292 |

* cited by examiner

METHODS FOR DETERMINING REACTIVE INDEX FOR CEMENTITIOUS COMPONENTS, ASSOCIATED COMPOSITIONS, AND METHODS OF USE

BACKGROUND

The present invention relates to cementitious components and, more particularly, in certain embodiments, to methods of determining a reactive index for cementitious components.

In general, well treatments include a wide variety of methods that may be performed in oil, gas, geothermal and/or water wells, such as drilling, completion and workover methods. The drilling, completion and workover methods may include, but are not limited to drilling, fracturing, acidizing, logging, cementing, gravel packing, perforating and conformance methods. Many of these well treatments are designed to enhance and/or facilitate the recovery of desirable fluids from a subterranean well. These fluids may include hydrocarbons such as oil and/or gas.

In cementing methods, such as well construction and remedial cementing, settable compositions are commonly utilized. As used herein, the term "settable composition" refers to a composition(s) that hydraulically sets or otherwise develops compressive strength. Settable compositions may be used in primary cementing operations whereby pipe strings, such as casing and liners, are cemented in well bores. In performing primary cementing, a settable composition may be pumped into an annulus between a subterranean formation and the pipe string disposed in the subterranean formation or between the pipe string and a larger conduit disposed in the subterranean formation. The settable composition should set in the annulus, thereby forming an annular sheath of hardened cement (e.g., a cement sheath) that should support and position the pipe string in the well bore and bond the exterior surface of the pipe string to the walls of the well bore or to the larger conduit. Settable compositions also may be used in remedial cementing methods, such as the placement of cement plugs, and in squeeze cementing for sealing voids in at pipe string, cement sheath, gravel pack, formation, and the like. Settable compositions may also be used in surface applications, for example, construction cementing.

Settable compositions for use in subterranean formations may typically include a cementitious component which hydraulically sets, or otherwise hardens, to develop compressive strength. Examples of cementitious components that can be included in settable compositions include Portland cement, calcium aluminate cement, cement kiln dust, lime kiln dust, fly ash, slag, pumice, and rice-hull ash, among others. The performance of these different cementitious components in settable compositions may vary and can even vary for as particular cementitious component depending, for example, on the particular type or source of the component. For example, certain of these cementitious components may have undesirable properties that can make them unsuitable for use in well treatments. In addition, variation of the performance for the cementitious components can lead to lack of predictability and consistency for the cementitious components when used in treatment fluids. This lack of predictability consistency may even be apparent for the same cementitious component, for example, if sourced from different locations.

SUMMARY

The present invention relates to cementitious components and, more particularly, in certain embodiments, to methods of determining a reactive index for cementitious components.

An embodiment discloses a method of cementing comprising: providing a settable composition comprising water and a cementitious component having a determined reactive index; and allowing the settable composition to set to form a hardened mass.

Another embodiment discloses a method of measuring reactivity of to cementitious component comprising: measuring a parameter of the cementitious component, the cementitious component having a specific surface area and dividing the measured parameter by the specific surface area of the cementitious component to obtain a reactive index for the cementitious component.

Another embodiment discloses a settable composition comprising: water; and a cementitious component having a calculated reactive index.

The features and advantages of the present invention will be readily apparent to those skilled in the art. While numerous changes may be made by those skilled in the art, such changes are within the spirit of the invention.

BRIEF DESCRIPTION OF THE DRAWINGS

These drawings illustrate certain aspects of some of the embodiments of the present invention, and should not be used to limit or define the invention.

DESCRIPTION OF PREFERRED EMBODIMENTS

The present invention relates to cementitious components and, more particularly, in certain embodiments, to methods of determining a reactive index for cementitious components. By determining the reactive index for cementitious components, blends of cementitious components may be used in well treatments, according to particular embodiments, that can provide more predictable and consistent performance. In addition, additional embodiments may include using the determined reactive index to provide blends of cementitious components in which one or more parameters have been optimized, including compressive strength, Young's Modulus, fluid loss, and/or thickening time, for example.

Without being limited by theory, the reactive index of a cementitious component may be referred to as a measure of the cementitious component's reactivity as adjusted for differences in surface area. Example techniques for determining the reactive index may comprise measuring a parameter of the cementitious component, and then dividing, the measured parameter by the specific surface area of the cementitious component. In some embodiments, the reactive index for a cementitious component may be calculated in accordance with the following equation:

$$RI=MP/SSA$$

wherein RI is the reactive index, MP is the measured parameter of the cementitious component, and SSA is the specific surface area of the cementitious component. In general, specific surface area is a property of a particulate solid and, as used herein, is defined as the total surface area of the cementitious component divided by the mass of the cementitious component or the total surface area divided by the bulk volume of the cementitious component.

In general, cementitious components are particulate solids that hydraulically set, or otherwise harden, to develop compressive strength in the presence of water. Non-limiting examples of cementitious components that may be suitable for use in embodiments of the present invention include Portland cements, calcium aluminate, gypsum, pozzolanic materials, and kiln dust. Mixtures of one or more different cementitious components may also be used. In some embodiments, the cementitious component may be combined with lime.

In some embodiments, the cementitious component may comprise Portland cement. Portland cement is a commonly used cementitious component that hydraulically reacts with water to develop compressive strength. Examples of suitable Portland cements may include those classified as Classes A, C, G and H cements according to American Petroleum Institute, *API Specification for Materials and Testing for Well Cements*, API Specification 10, Fifth Edition, Jul. 1, 1990. In addition, Portland cements suitable for use in embodiments of the present invention may also include those classified as ASTM Type I, II, II, III, IV, or V. In some embodiments, blends of cementitious components containing Portland cement may be used.

In some embodiments, the cementitious component may comprise a calcium aluminate. Calcium aluminate may hydraulically react with water to develop compressive strength. Calcium aluminate may be included in cements commonly referred to as calcium aluminate cements or high alumina content cements. Calcium aluminate cements may be prepared in a manufacturing process that includes mixing a calcium bearing material (e.g., limestone) and an aluminum-bearing material (e.g., bauxite).

In some embodiments, the cementitious component may comprise gypsum. Gypsum is a material that sets in the presence of water to develop compressive strength. Gypsum may be included in cements commonly referred to as gypsum cements. For use in cements, gypsum may, in some instances, be burned at extremely high temperatures and then ground. In particular embodiments, gypsum may be added to Portland cement.

In some embodiments, the cementitious component may comprise a pozzolanic material. Pozzolanic materials that may be suitable for use include a wide variety of natural or artificial materials that exhibit cementitious properties in the presence of calcium hydroxide. Examples of suitable pozzolanic material that may be suitable for use in embodiments of the present invention include natural and artificial pozzolans, such as fly ash, silica fume, slag, burned shale, burned clay, metakaolin, pumice, diatomaceous earth, volcanic ash, opaline shale, tuff, and burned organic materials, such as agricultural waste ash, municipal waste ash (e.g., municipal solid waste ash), waste-water treatment waste ash, animal waste ash, non-human-non-animal industrial waste ash, and combinations thereof. Specific examples of agricultural waste ash include, for example, rice husk ash, wood (e.g., sawdust, bark, twigs, branches, other waste wood) ash, tree leave ash, corn cob ash, cane (e.g., sugar cane) ash, bagasse ash, grain (e.g., amaranth, barley, corn flaxseed, millet, oat, quinoa, rye, wheat etc.) and related by-product(s) (e.g., husks, hulls, etc.) ash, orchard ash, vine trimming ash, grass (e.g., Korai, Tifton, native shiba, etc.) ash, straw ash, ground nut shell ash, legume (e.g., soybean) ash, and combinations thereof.

In some embodiments, the cementitious component may comprise a kiln dust. One example of a kiln dust includes cement kiln dust. Cement kiln dust, as that term is used herein, refers to a partially calcined kiln feed which is removed from the gas stream and collected, for example, in a dust collector during the manufacture of cement. The cement kiln dust generally may exhibit cementitious properties, in that it may set and harden in the presence of water. Usually, large quantities of cement kiln dust are collected in the production of cement that are commonly disposed of as waste. Disposal of the cement kiln dust can add undesirable costs to the manufacture of the cement, as well as the environmental concerns associated with its disposal. The chemical analysis of the cement kiln dust from various cement manufactures varies depending on a number of factors, including the particular kiln feed, the efficiencies of the cement production operation, and the associated dust collection systems. Cement kin dust generally may comprise a variety of oxides, such as $SiO_2$, $Al_2O_3$, $Fe_2O_3$, $CaO$, $MgO$, $SO_3$, $Na_2O$, and $K_2O$. Another example of a kiln dust includes lime kiln dust. Lime kiln dust, as that term is used herein, refers to a product generated in the manufacture of lime. The lime kiln dust may be collected, for example, by dust control systems in the calcination of lime stone.

In some embodiments, one or more parameters of the cementitious component may be measured and then used in determining the reactive index. The parameters may include a number of different parameters that may be measured using standard laboratory testing techniques for a settable composition comprising a cementitious component and water. Additional components may also be included in the settable compositions, for example, to vary one or more properties of the treatment fluid. Parameters of the cementitious component, or settable composition contained therein, that may be measured include, for example, compressive strength, Young's Modulus, fluid loss, thickening time, rheological values (e.g., volume average apparent viscosity, plastic viscosity, yield point, etc.) and/or free water.

Compressive strength is generally the capacity of a material or structure to withstand axially directed pushing forces. The compressive strength of the cementitious component may be measured at a specified time after the cementitious component has been mixed with water and the resultant treatment fluid is maintained under specified temperature and pressure conditions. For example, compressive strength can be measured at a time in the range of about 24 to about 48 hours after the fluid is mixed and the fluid is maintained at a temperature of 170° F. and atmospheric pressure. Compressive strength can be measured by either a destructive method or non-destructive method. The destructive method physically tests the strength of treatment fluid samples at various points in time by crushing the samples in a compression-testing machine. The compressive strength is calculated from the failure load divided by the cross-sectional area resisting the load and is reported in units of pound-force per square inch (psi). Non-destructive methods typically may employ an Ultrasonic Cement Analyzer ("UCA"), available from Fann Instrument Company, Houston, Tex. Compressive strengths may be determined in accordance with API RP 10B-2, *Recommended Practice for Testing Well Cements*, First Edition, July 2005.

Young's modulus also referred to as the modulus of elasticity is a measure of the relationship of an applied stress to the resultant strain. In general, a highly deformable (plastic) material will exhibit a lower modulus when the confined stress is increased. Thus, the Young's modulus is an elastic constant that demonstrates the ability of the tested material to withstand applied loads. A number of different laboratory techniques may be used to measure the Young's modulus of a treatment fluid comprising a cementitious component after the treatment fluid has been allowed to set for a period of time at specified temperature and pressure conditions.

Fluid loss typically refers to loss of a fluid such as a treatment fluid into a subterranean formation. A number of different laboratory techniques may be used to measure fluid loss of a treatment fluid to give an indication of the behavior of the treatment fluid in a well. Fluid loss may be measured using a static fluid-loss test, with either a static or stirred fluid-loss cell, in accordance with the afore-mentioned API RP Practice 10B-2.

Thickening time typically refers to the time a fluid, such as a treatment fluid, comprising the cementitious component, remains in a fluid state capable of being pumped. A number of different laboratory techniques may be used to measure thickening time to give an indication of the amount of time a treatment fluid will remain pumpable in a well. An example technique for determining whether a treatment fluid is in a pumpable fluid state may use a high-temperature high-pressure consistometer at specified pressure and temperature conditions, in accordance with the procedure for determining cement thickening times set forth in the afore-mentioned API RP Practice 10B-2. The thickening time may be the time for the treatment fluid to reach 70 Bearden units of consistency ("Bc") and may be reported in time to reach 70 Bc.

Rheological values of a fluid may be determined to characterize the fluid's rheological behavior. Rheological values that may be determined include volume average apparent viscosity, yield point and plastic viscosity, among others. Plastic viscosity is typically a measure of the resistance of a fluid to flow. In some embodiments, the yield point may be a parameter of the Bingham plastic model, the yield point being the slope of the shear stress/shear rate line above the yield point. Yield point is typically a measure of the point at which a material can no longer deform elastically. In some embodiments, the yield point may be a parameter of the Bingham plastic model, the yield point being the yield stress extrapolated to a shear rate of zero. A number of different laboratory techniques may be used to measure theological values of a treatment fluid to give an indication of the behavior of the treatment fluid in a well. Rheological values may be determined in accordance with the procedure set forth in API RP Practice 10B-2.

Free water typically refers to any water in a fluid that is in excess to what is required to fully hydrate the components of the fluid. Free water can be undesired as it may physically separate from a cement composition as it sets. Free water may also be referred to as free fluid. A number of different laboratory techniques may be used to measure free water of a treatment fluid to give an indication of the behavior of the treatment fluid in a well. Free water may be determined in accordance with the procedure set forth in API RP Practice 10B-2.

As previously mentioned, the reactivity of cementitious components may vary between different types of cementitious components or even between different sources for a particular type of cementitious component. For example, the reactivity of Portland cement and another cementitious component, such as a pozzolanic material, may be different. By way of further example, the reactivity of a cementitious component may vary between different sources for the cementitious component. In some embodiments, the reactive index of the cementitious component may vary between two or more different sources by a factor of at least about 2:1. For example, the reactive index of the cementitious component between different sources may vary by an amount between any of and/or including any of about 2:1, about 10:1, about 50:1, about 100:1, about 250:1, about 500:1, or about 1000:1. Because the reactivity varies between different cementitious components and even between different sources for a cementitious component, the performance of different cementitious components may be unpredictable and may also lead to a lack of consistency for the cementitious components when used in treatment fluids such as settable compositions. In some instances, the performance of a particular cementitious component may have undesirable properties, which may make it unsuitable for use. For example, a cementitious component from a particular source may have properties making it undesirable for use.

In some embodiments, a blend of two or more different cementitious components may be used to provide a blended cementitious component that may have properties suitable for use in a particular application. This may be particularly useful, for example, where one of the cementitious components in the blend may have properties making it unsuitable for particular applications. For example, a cementitious component such as cement kiln dust from a first source may be blended with a cementitious component such as cement kiln dust from a second source. In some embodiments, one or both of the cementitious components may have reactivities that are unsuitable for a particular application. For example, the reactivities of each cementitious component may be individually too slow or too fast for a particular application. The blends of the cementitious component from the two different sources may form a blended cementitious component having compressive strength properties that are suitable for the application. In some embodiments, the relative proportions (e.g., weight fractions) of each cementitious component in the blended cementitious component may then be adjusted to adjust the compressive strength properties of the blended cementitious component.

The two or more cementitious components in the blended cementitious component may include, for example, two or more different types of cementitious components, such as Portland cement and cement kiln dust. Alternatively, the two or more cementitious components in the blended cementitious component may include, for example, a cementitious component from two or more different sources. For example, a first cementitious component may comprise cement kiln dust from a first source, and the second cementitious component may comprise cement kiln dust from a second source. It should be understood that embodiments are not limited to only two different sources, but may include a cementitious component, such as cement kiln dust, from three, four, five, or even more different sources. The two or more different sources for the cementitious component may include different manufactures, different cement manufacturing plants, and the like. A cementitious component, such as cement kiln dust which is a byproduct from the cement manufacturing plant, may have a number of different sources available throughout the world. For example, different sources for cement kiln dust may include different manufacturing plants throughout the world at which cement kiln dust can be generated.

The two or more cementitious components may be blended to form the blended cementitious component, for example, prior to combination with water and/or other components of the treatment fluid. In particular embodiments, the two or more cementitious components may be dry blended to form a dry blend comprising the two or more cementitious components. The dry blend may then be combined with water and/or other components, in any order, to form the treatment fluid. However, the use of the term "blend" is not intended to imply that the two or more cementitious components have been dry blended prior to combination with water. For example, the blend of two or more cementitious components may not be combined until after one, or even both, of the cementitious components has already been blended with water.

In some embodiments, the reactive index may be used to optimize the blended cementitious component, wherein the blended cementitious component comprises two or more cementitious components. For example, the reactive index may be used to optimize one or more parameters of the blended cementitious component, including compressive strength, Young's Modulus, fluid loss, and/or thickening time. Optimizing the blended cementitious component may include determining the reactive index for each of the cementitious components in the blended cementitious component. The reactive indexes for the cementitious components may then be used to predict the performance of the blended cementitious component. The ratio of each cementitious component may be adjusted to optimize the performance of the blended cementitious component. The performance of the blended cementitious component may be optimized with the performance of the blended cementitious component estimated using the following equation:

$$EP_{blend} = \sum_{i=1}^{n} (RI_i)(SSA_i)(f_i)^m$$

Wherein $EP_{blend}$ is the estimated parameter for the blended cementitious component, i is the individual cementitious component from the set of cementitious components 1 to n, n is an integer, $RI_i$ is the reactive index for cementitious component i, $SSA_i$ is the specific surface area for cementitious component i, $f_i$ is the mass fraction of the cementitious component i, and wherein m is a number from 1 to 10. The set of cementitious components may include 2 or more different cementitious components. The two or more different cementitious component may be different types of cementitious components, such as Portland cement and slag, or may be from different sources, such as cement kiln dust from a first source and cement kiln dust from a second source. In some embodiments, m may be 1. In alternative embodiments, m may be 7/3.

In some embodiments, the mean particle size of the cementitious component may be altered from its original particle size. The reactive index may then be measured for the altered cementitious component. The altered cementitious component may be included in a blended cementitious component. In accordance with present embodiments, the mean particle size of the cementitious component can be altered using any suitable technique, including, without limitation, grinding or separating to provide a material having an altered particle size. Separating the cementitious component may include sieving or any other suitable technique for separating the cementitious component to provide a mean particle size that has been altered from its original size. For example, sieving may be used to produce cementitious component having an increased or reduced mean particle size as desired for a particular application. By way of further example, grinding may be used to decrease the mean particle size of the cementitious component. Combinations of grinding and separating may be used in some embodiments. The term "ground" or "grinding" as used herein means using a grinder (e.g., ball mill, rod mill, etc.) to reduce the particle size of the specified component(s). An example of a suitable grinder is an 8000 Mixer/Mill® ball mill, available from SPEX Sample Prep. In some embodiments, the cementitious component may be ground for a time period in a range of from about 30 minutes to about 1 hour.

The mean particle size of the cementitious component can be altered to any size suitable for use in cementing operations. In some embodiments, the mean particle size of the cementitious component may be altered from its original particle size to have a mean particle size in a range of about 1 micron to about 350 microns. The mean particle size corresponds to d50 values as measured by particle size analyzers such as those manufactured by Malvern Instruments, Worcestershire, United Kingdom.

In some embodiments, the mean particle size of the cementitious component may be increased from its original size. For example, the mean particle size of the cementitious component may be at least 5% greater than its original size. In some embodiments, at least a portion of the cementitious component may be increased to a size that is in a range of from about 5% to about 500% greater than its original size. In some embodiments, the mean particle size may be increased to a size ranging between any of and/or including any of about 5%, about 10%, about 20%, about 30%, about 40%, about 50%, about 60%, about 70%, about 80%, about 90%, about 100%, about 200%, about 300%, about 400%, or about 500% greater than its original size.

In some embodiments, the mean particle size of the cementitious component may be reduced from its original size. For example, the mean particle size may be reduced in an amount sufficient to increase the compressive strength of the cementitious component. In some embodiments, the cementitious component may have a mean particle size that is at least 5% less than its original size. In some embodiments, at least a portion of the cementitious component may be reduced to have a mean particle size in a range of from about 5% to about 95% of its original size. For example, the mean particle size may be reduced to a size ranging between any of and/or including any of about 5%, about 10%, about 15%, about 20%, about 25%, about 30%, about 35%, about 40%, about 45%, about 50%, about 55%, about 60%, about 6%, about 70%, about 75%, about 80%, about 90%, or about 95% of its original size. By way of example, the reduced particle size cementitious component may have a mean particle size of less than about 15 microns. In some embodiments, the reduced particle size cementitious component may have a mean particle size of less than about 10 microns, less than about 5 microns, less than about 4 microns, less than about 3 microns, less than about 2 microns, or less than about 1 micron. In specific embodiments, the reduced particle size cementitious component may have a mean particle size in a range of from about 0.1 microns to about 15 microns, from about 0.1 microns to about 10 microns, or from about 1 micron to about 10 microns. One of ordinary skill in the art, with the benefit of this disclosure, should be able to select a particle size for the cementitious component suitable for a particular application.

In some embodiments, the mean particle size of the cement kiln dust may be reduced in an amount sufficient to provide an increase in compressive strength for the settable composition. For example, the mean particle size may be reduced to provide an increase in compressive strength of at least about 5%, about 25%, about 50%, about 75%, or about 100%.

In accordance with present embodiments, the cementitious components may be included in treatment fluids that can be used in a variety of operations that may be performed in subterranean formations. The cementitious component may have reactive index calculated according to disclosed embodiments. In some embodiments, a blended cementitious component may be used. In some embodiments, the reactive index may be used in determining the cementitious components in a particular blended cementitious component. As referred to herein, the term "treatment fluid" will be understood to mean any fluid that may be used in a subterranean application in conjunction with a desired function and/or for a desired purpose. The term "treatment fluid" is not intended to imply any particular action by the fluid. Treatment fluids often are used in, e.g., well drilling, completion, and stimulation operations. Examples of such treatment fluids include drilling fluids, well cleanup fluids, workover fluids, conformance fluids, gravel pack fluids, acidizing fluids, fracturing fluids, cement compositions, spacer fluids, and the like.

While embodiments of the compositions and methods may be used in a variety of applications, they may be particularly useful for subterranean well completion and remedial operations, such as primary cementing of casings and liners in well bores. They also may be useful for surface cementing operations, including construction cementing operations. Accordingly, embodiments of the present invention disclose settable compositions comprising a cementitious component and water.

The cementitious component may be included in embodiments of the settable compositions in an amount suitable for a particular application. In some embodiments, the cementitious component may comprise cement kiln dust. The cement kiln dust may be present in an amount in a range of from about 0.01% to 100% by weight of the cementitious component ("bwoc"). For example, the cement kiln dust may be present in an amount ranging between any of and/or including any of about 0.01%, about 5%, about 10%, about 20%, about 30%, 40%, about 50%, about 60%, about 70%, about 80%, about 90%, or about 100%. The cementitious component may be free or essentially free (for example, no more than 1% by weight of the cementitious component) of any additional cementitious components other than the cementitious component. In some embodiments, the cementitious component may be essentially free of Portland cement. One of ordinary skill in the art with the benefit of this disclosure should be able to determine an appropriate amount of the cementitious component to include for a particular application.

The water used in embodiments of the settable compositions of the present invention may include, for example, freshwater, saltwater (e.g., water containing one or more salts dissolved therein), brine (e.g., saturated saltwater produced from subterranean formations), seawater, or any combination thereof. Generally, the water may be from any source, provided, for example, that it does not contain an excess of compounds that may undesirably affect other components in the settable composition. In some embodiments, the water may be included in an amount sufficient to form a pumpable slurry. In some embodiments, the water may be included in the settable compositions of the present invention in an amount in a range of from about 40% to about 200% bwoc. For example, the water may be present in an amount ranging between any of and/or including any of about 50%, about 75%, about 100%, about 125%, about 150%, or about 175% by weight of the cement. In specific embodiments, the water may be included in an amount in the range of from about 40% to about 150% bwoc. One of ordinary skill in the art, with the benefit of this disclosure, will recognize the appropriate amount of water to include for a chosen application.

Other additives suitable for use in subterranean cementing operations may also be added to embodiments of the settable compositions, in accordance with embodiments of the present invention. Examples of such additives include, but are not limited to, fluid-loss-control additive, set retarder, strength-retrogression additives, set accelerators, weighting agents, lightweight additives, gas-generating additives, mechanical-property-enhancing additives, lost-circulation materials, filtration-control additives, foaming additives, thixotropic additives, and any combination thereof. Specific examples of these, and other, additives include crystalline silica, amorphous silica, fumed silica, salts, fibers, hydratable clays, calcined shale, vitrified shale, microspheres, hollow glass spheres, fly ash, diatomaceous earth, metakaolin, ground perlite, rice husk ash, natural pozzolan, zeolite, cement kiln dust, resins, any combination thereof, and the like. A person having ordinary skill in the art, with the benefit of this disclosure, will readily be able to determine the type and amount of additive useful for a particular application and desired result.

Those of ordinary skill in the art will appreciate that embodiments of the settable compositions generally should have a density suitable for a particular application. By way of example, embodiments of the settable compositions may have a density of about 4 pounds per gallon ("lb/gal") to about 20 lb/gal. In certain embodiments, the settable compositions may have a density of about 8 lb/gal to about 17 lb/gal. Embodiments of the settable compositions may be foamed or unfoamed or may comprise other means to reduce their densities, such as hollow microspheres, low-density elastic beads, or other density-reducing additives known in the art. In addition, the settable composition may comprise weighting agents or other means to increase their densities. Those of ordinary skill in the art, with the benefit of this disclosure, will recognize the appropriate density for a particular application.

In some embodiments, the settable compositions may have a thickening time of greater than about 1 hour, alternatively, greater than about 2 hours, alternatively greater than about 5 hours at 3,000 psi and temperatures in a range of from about 50° F. to about 400° F., alternatively, in a range of from about 80° F. to about 250° F., and alternatively at a temperature of about 140° F. In some embodiments, the settable composition may have a 24-hour compressive strength in a range of from about 100 psi to about 10,000 psi and, alternatively, from about 350 psi about 3,000 psi at atmospheric pressure and temperatures in a range of from about 50° F. to about 400° F., alternatively, in a range of from about 80° F. to about 250° F., and alternatively at a temperature of about 180° F.

The components of the settable composition may be combined in any order desired to form a settable composition that can be placed into a subterranean formation. In addition, the components of the settable compositions may be combined using any mixing device compatible with the composition, including a bulk mixer, for example. In some embodiments, a dry blend may first be formed by the cementitious component or mixture of cementitious components. The dry blend may then be combined with water to form the settable composition. Other suitable techniques may be used for preparation of the settable compositions as will be appreciated by those of ordinary skill in the art in accordance with embodiments of the present invention.

As will be appreciated by those of ordinary skill in the art, embodiments of the cement compositions of the present invention may be used in a variety of cementing operations, including surface and subterranean operations, such as primary and remedial cementing. In some embodiments, a cement composition may be provided that comprises a cementitious component and water, and allowed set. In certain embodiments, the cement composition may be introduced into a subterranean formation and allowed to set therein. As used herein, introducing the cement composition into a subterranean formation includes introduction into any portion of the subterranean formation, including, without limitation, into a well bore drilled into the subterranean formation, into a near well bore region surrounding the well bore, or into both.

In primary-cementing embodiments, for example, embodiments may comprise providing a cement composition, introducing the cement composition into a well-bore annulus; and allowing the cement composition to set in the annulus to form a hardened mass. The well-bore annulus may include, for example, an annular space between a conduit (e.g., pipe string, liner, etc.) and a wall of a well bore or between the conduit and a larger conduit in the well bore. Generally, in most instances, the hardened mass should fix the conduit in the well bore.

In remedial-cementing embodiments, a cement composition may be used, for example, in squeeze-cementing operations or in the placement of cement plugs. By way of example, the cement composition may be placed in a well bore to plug an opening, such as a void or crack in the formation, in a gravel pack, in the conduit, in the cement sheath, and/or a microannulus between the cement sheath and the conduit or formation. An example of such a method may comprise placing the cement composition into the void, and allowing the cement composition to set in the void.

While the preceding description is directed to the use of the cementitious component in cementing methods, it should be understood that embodiments of the present technique also encompasses the use of the cementitious component in any of a variety of different subterranean treatments. The cementitious component may have a reactive index determined according to disclosed embodiments. In some embodiments, a blended cementitious component may be used. In some embodiments, the reactive index may be used in determining the amount of cementitious components that are in a particular blended cementitious component. An example method may include a subterranean treatment method that comprises providing a treatment fluid comprising the cementitious component and introducing the treatment fluid into a subterranean formation. For example, a drilling fluid may comprise the cementitious component, wherein the drilling fluid may be circulated downwardly through a drill pipe and drill bit and then upwardly through the well bore to the surface. The drilling fluid used may be any number of fluids (gaseous or liquid) and mixtures of fluids and solids (such as solid suspensions, mixtures, and emulsions).

In some embodiments, a spacer fluid may comprise the cementitious component, which may have a determined reactive index according to disclosed embodiments. Spacer fluids may be used, for example, in the displacement of fluids from well bore. In an embodiment, the fluid displaced by the spacer fluid comprises a drilling fluid. By way of example, the spacer fluid may be used to displace the drilling fluid from the well bore. The drilling fluid may include, for example, any number of fluids, such as solid suspensions, mixtures, and emulsions. Additional steps in embodiments of the method may comprise introducing a pipe string into the well bore, introducing a cement composition into the well bore with the spacer fluid separating the cement composition and the first fluid. In an embodiment, the cement composition may be allowed to set in the well bore. The cement composition may include, for example, cement and water. In some embodiments, at least a portion of the spacer fluid may be left in the well bore, the spacer fluid in the well bore setting to form a hardened mass.

EXAMPLES

To facilitate a better understanding of the present invention, the following examples of certain aspects of some embodiments are given. In no way should the following examples be read to limit, or define, the entire scope of the invention.

Example 1

Figure 1:
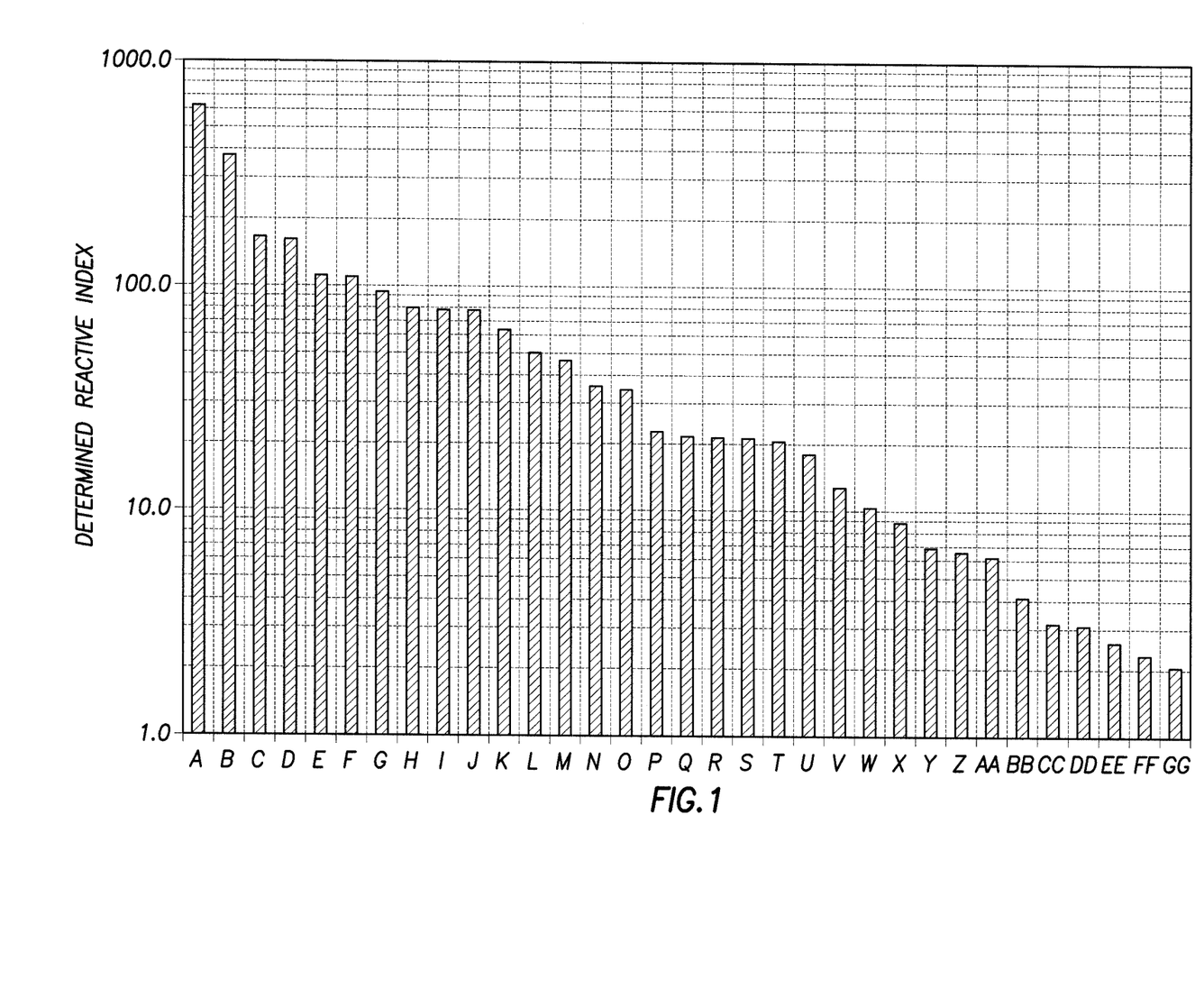
FIG. 1 is a chart showing measured reactive indexes for various supply sources of cement kiln dust.

The reactive indexes for compressive strength for thirty-three different samples of cement kiln dust, designated Samples A through GG, were determined and are provided in FIG. 1. The CKD samples are each from a different supply source. The reactive indexes for thirty-three CKD samples were determined by dividing the determined 24-hour compressive strength for a settable composition by the specific surface area of the CKD sample. The specific surface area for each CKD sample was determined by dividing the total surface area of the particular CKD sample by the sample mass. The surface area was determined using a Malvern particle size analyzer. The 24-hour compressive strength for each CKD sample was determined by first preparing a settable composition that comprised the CKD sample in an amount of 100% bwoc and water in an amount sufficient to provide a density of about 13 lb/gal. After preparation, the settable composition was allowed to cure for 24 hours in a 2"×4" metal cylinder that was placed in a water bath at 170° F. to form set cement cylinders. Immediately after removal from the water bath, destructive compressive strengths were determined using a mechanical press in accordance with API RP 10B-2.

Example 2

Blended cementitious components were prepared that comprised mixtures of the CKD samples from Example 1, as indicated in the table below. The determined reactive indexes for the CKD samples were then used in the following equation to predict the performance of each blended cementitious component.

$$CS_{blend} = (RI_Z)(SSA_Z)(f_Z)^m + (RI_F)(SSA_F)(f_F)^m + (RI_E)(SSA_E)(f_E)^m$$

Wherein $CS_{blend}$ is the estimated compressive strength for the blended cementitious component, $RI_Z$ is the reactive index for compressive strength for CKD Sample Z and was 6.9, m is 1, $SSA_Z$ is the specific surface area for CKD Sample Z and was 2.32, $f_Z$ is the mass fraction of CKD Sample Z, $RI_F$ is the reactive index for compressive strength for CKD Sample F and was 105, $SSA_F$ is the specific surface area for CKD Sample F and was 2.33, $f_F$ is the mass fraction of CKD Sample F, $RI_E$ is the reactive index for compressive strength for CKD Sample E and was 107, $SSA_E$ is the specific surface area for CKD Sample E and was 3.6, and $f_E$ is the mass fraction of CKD Sample E.

The estimated compressive strength values for the blended cementitious components were then compared with the actual 24-hour compressive strength values for the blended cementitious components. The 24-hour compressive strength for each blended cementitious component was determined by first preparing a settable composition that comprised the blended cementitious component in an amount of 100% bwoc and water in an amount sufficient to provide a density of 13 lb/gal. A cement dispersant (CFR-3™ cement friction reducer, from Halliburton Energy Services, Inc.) in an amount of from 0.5% bwoc to 1.0% bwoc was added to some of the samples and should not impact determined compressive strength values. After preparation, the settable composition was allowed to cure for 24 hours in a 2"×4" metal cylinder that was placed in a water bath at 140° F. to form set cement cylinders. Immediately after removal from the water bath, destructive compressive strengths were determined using a mechanical press in accordance with API RP 10B-2.

Figure 2:
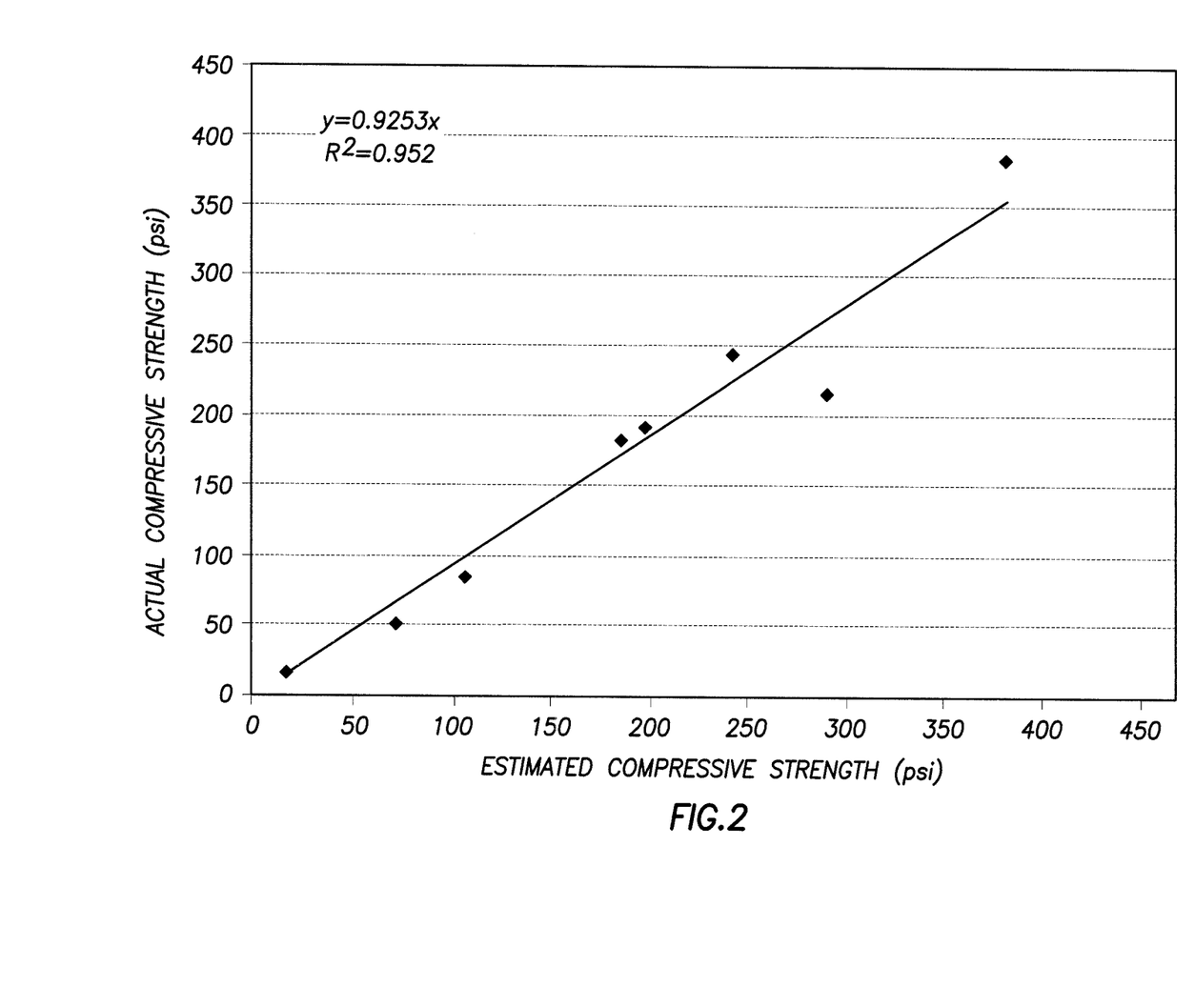
FIG. 2 is a chart comparing actual versus predicted compressive strength for dry blends of cement kiln dust.

A chart of the actual compressive strength values versus the estimated compressive strength values is provided on FIG. 2. As shown on FIG. 2, the charted values have an $R^2$ value of 10.952 and a slope of 0.9253. The estimated and actual compressive strength values for the blended cementitious components are also provided in Table 1 below.

TABLE 1

| CKD Sample Z (% bwoc) | CKD Sample F (% bwoc) | CKD Sample E (% bwoc) | Estimated Compressive Strength (psi) | Actual Compressive Strength (psi) |
|---|---|---|---|---|
| 100 | 0 | 0 | 16 | 16 |
| 75 | 25 | 0 | 73 | 51 |
| 25 | 75 | 0 | 187 | 183 |
| 0 | 100 | 0 | 244 | 244 |
| 75 | 0 | 25 | 108 | 84 |
| 50 | 0 | 50 | 200 | 192 |
| 25 | 0 | 75 | 292 | 216 |
| 0 | 0 | 100 | 384 | 384 |

Example 3

The reactive indexes for volume average apparent viscosity at 511 sec$^{-1}$ and 51 sec$^{-1}$ were determined for CKD Samples Z, F, and E from Example 1 and are provided in Table 2 below. The reactive indexes for these samples were determined by dividing the determined volume average apparent viscosity for a settable composition by the specific surface area of the CKD sample. The specific surface area for each CKD sample was determined by dividing the total surface area of the particular CKD sample by the sample mass. The surface area was determined using a Malvern particle size analyzer. The 24-hour volume average apparent viscosity ("VAV") for each CKD sample was determined by first preparing a settable composition that comprised the CKD sample in an amount of 100% bwoc and water in an amount sufficient to provide a density of about 12 lb/gal. The volume average apparent viscosities were measured at 511 1 sec$^{-1}$ and 51 sec$^{-1}$ in accordance with API RP 10B-2.

TABLE 2

|  | CKD Sample Z | CKD Sample F | CKD Sample E |
|---|---|---|---|
| SSA | 2.32 | 2.33 | 3.6 |
| VAV at 511 sec$^{-1}$ (cp) | 11 | 62 | 123 |
| RI at 511 sec$^{-1}$ | 5 | 27 | 32 |
| VAV at 51 sec$^{-1}$ (cp) | 40 | 410 | 860 |
| RI at 51 sec$^{-1}$ | 17 | 176 | 239 |

Next, blended cementitious components were prepared that comprised mixtures of CKD samples Z, F, E, as indicated in the table below. The determined reactive indexes at 511 sec$^{-1}$ and 51 sec$^{-1}$ for the CKD samples were then used in the following equation to predict the performance of each blended cementitious component.

$$VAV_{blend} = (RI_Z)(SSA_Z)(f_Z)^m + (RI_F)(SSA_F)(f_F)^m + (RI_E)(SSA_E)(f_E)^m$$

Wherein $VAV_{blend}$ is the estimated volume average apparent viscosity for the blended cementitious component, $RI_Z$ is the reactive index for volume average apparent viscosity for CKD Sample Z, $SSA_Z$ is the specific surface area for CKD Sample Z, $f_Z$ is the mass fraction of CKD Sample Z, m is 7/3. $RI_F$ is the reactive index for volume average apparent viscosity for CKD Sample F, $SSA_F$ is the specific surface area for CKD Sample F, $f_Z$ is the mass fraction of CKD Sample F, $RI_E$ is the reactive index for volume average apparent viscosity for CKD Sample E, $SSA_E$ is the specific surface area for CKD Sample E, and $f_E$ is the mass fraction of CKD Sample E.

The estimated volume average apparent viscosities at 511 sec$^{-1}$ and 51 sec$^{-1}$ for the blended cementitious components were then compared with the actual volume average apparent viscosities at 511 sec$^{-1}$ and 51 sec$^{-1}$ for the blended cementitious components. The volume average apparent viscosities for each blended cementitious component was determined by first preparing a settable composition that comprised the blended cementitious component in an amount of 100% bwoc and water in an amount sufficient to provide a density of 12 lb/gal. After preparation, the volume average apparent viscosities at 511 sec$^{-1}$ and 51 sec$^{-1}$ were determined in accordance with API RP 10B-2.

Figure 3:
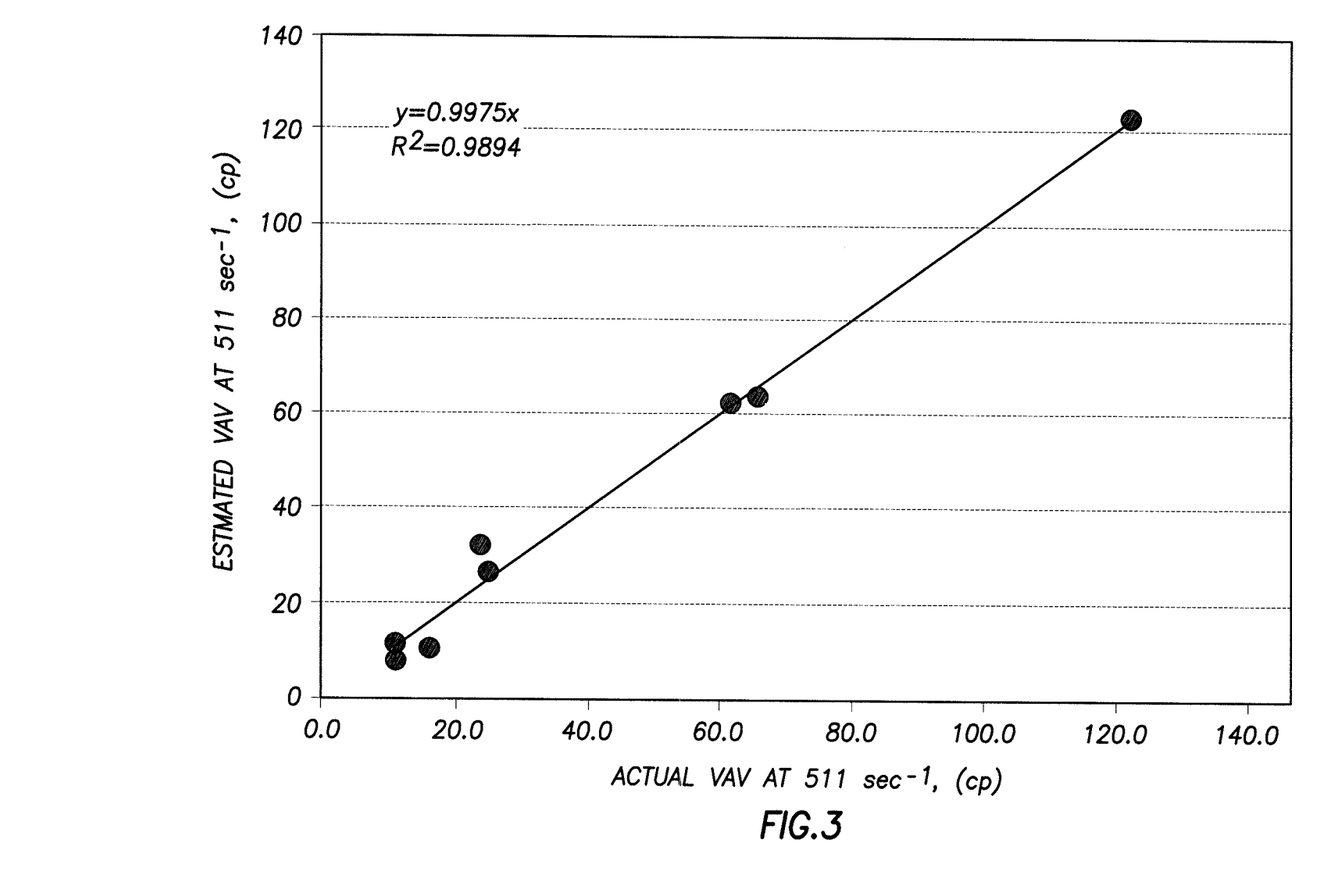
FIG. 3 is a chart comparing, actual versus predicted volume average apparent viscosity at 511 $sec^{-1}$ for dry blends of cement kiln dust.
Figure 4:
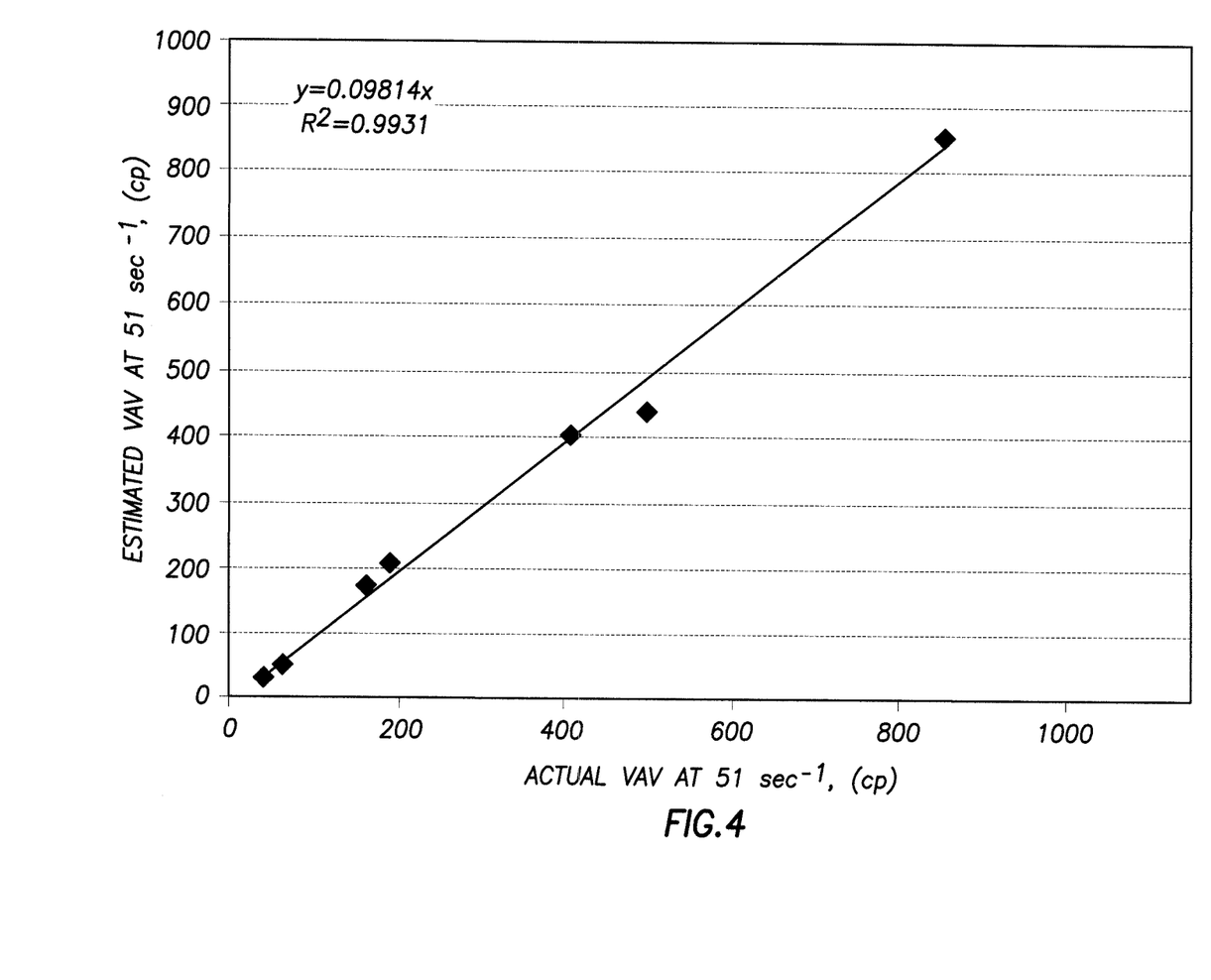
FIG. 4 is a chart comparing actual versus predicted volume average apparent viscosity at 51 $sec^{-1}$ for dry blends of cement kiln dust.

Charts of the actual volume average viscosity values versus the estimated volume average viscosity values are provided on FIGS. 3 and 4. As shown on FIG. 3, the charted values at 511 sec$^{-1}$ have an $R^2$ value of 0.9894 and a slope of 0.9975. As shown on FIG. 4, the charted values at 51 sec$^{-1}$ have an $R^2$ value of 0.9931 and a slope of 0.9814. The estimated and actual volume average viscosity values for the blended cementitious components are also provided in Table 2 below.

TABLE 3

| CKD Sample Z (% bwoc) | CKD Sample F (% bwoc) | CKD Sample E (% bwoc) | Actual VAV @ 511 sec$^{-1}$ (cp) | Est. VAV @ 511 sec$^{-1}$ (cp) | Actual VAV @ 51 sec$^{-1}$ (cp) | Est. VAV @ 51 sec$^{-1}$ (cp) |
|---|---|---|---|---|---|---|
| 100 | 0 | 0 | 11.0 | 11.0 | 40.0 | 40.0 |
| 75 | 25 | 0 | 11.0 | 8.1 | 40.0 | 36.7 |
| 25 | 75 | 0 | 24.0 | 32.2 | 190.0 | 211.3 |
| 0 | 100 | 0 | 62.0 | 62.0 | 410.1 | 410.0 |
| 0 | 0 | 100 | 123.0 | 123.0 | 860.2 | 860.0 |
| 25 | 0 | 75 | 66.0 | 63.4 | 500.1 | 441.5 |
| 50 | 0 | 50 | 25.0 | 26.7 | 160.0 | 179.0 |
| 75 | 0 | 25 | 16.0 | 10.5 | 60.0 | 54.5 |

It should be understood that the compositions and methods are described in terms of "comprising," "containing," or "including" various components or steps, the compositions and methods can also "consist essentially of" or "consist of" the various components and steps. Moreover, the indefinite articles "a" or "an," as used in the claims, are defined herein to mean one or more than one of the element that it introduces.

For the sake of brevity, only certain ranges are explicitly disclosed herein. However, ranges from any lower limit may be combined with any upper limit to recite a range not explicitly recited, as well as, ranges from any lower limit may be combined with any other lower limit to recite a range not explicitly recited, in the same way, ranges from any upper limit may be combined with any other upper limit to recite a range not explicitly recited. Additionally, whenever a numerical range with a lower limit and an upper limit is disclosed, any number and any included range falling within the range are specifically disclosed. In particular, every range of values (of the form, "from about a to about b," or, equivalently, "from approximately a to b," or, equivalently, "from approximately a-b") disclosed herein is to be understood to set forth every number and range encompassed within the broader range of values even if not explicitly recited. Thus, every point or individual value may serve as its own lower or upper limit combined with any other point or individual value or any other lower or upper limit, to recite a range not explicitly recited.

Therefore, the present invention is well adapted to attain the ends and advantages mentioned as well as those that are inherent therein. The particular embodiments disclosed above are illustrative only, as the present invention may be modified and practiced in different but equivalent manners apparent to those skilled in the art having the benefit of the teachings herein. Although individual embodiments are discussed, the invention covers all combinations of all those embodiments. Furthermore, no limitations are intended to the details of construction or design herein shown, other than as described in the claims below. Also, the terms in the claims have their plain, ordinary meaning unless otherwise explicitly and clearly defined by the patentee. It is therefore evident that the particular illustrative embodiments disclosed above may be altered or modified and all such variations are considered within the scope and spirit of the present invention. If there is any conflict in the usages of a word or term in this specification and one or more patent(s) or other documents that may be incorporated herein by reference, the definitions that are consistent with this specification should be adopted.

What is claimed is:

1. A method of cementing comprising:
   providing a settable composition comprising water and a cementitious component having a determined reactive index; wherein the particle size of the cementitious component has been adjusted to adjust the determined reactive index; and
   allowing the settable composition to set to form a hardened mass.

2. The method of claim 1 wherein the settable composition has a density in a range of about 4 pounds per gallon to about 20 pounds per gallon.

3. The method of claim 1 wherein the water is present in an amount sufficient to form a pumpable slurry.

4. The method of claim 1 wherein the cementitious component comprises at least one component selected from the group consisting of Portland cement, calcium aluminate, gypsum, a pozzolanic material, kiln dust, and any combination thereof.

5. The method of claim 1 wherein the settable composition further comprises a second cementitious component, wherein the cementitious component and the second cementitious component have different reactive indexes.

6. The method of claim 5 wherein the cementitious component and the second cementitious component have reactive indexes that vary by a factor of at least about 2:1.

7. The method of claim 5 wherein the cementitious component and the second cementitious component have reactive indexes that vary by a factor of at least about 100:1.

8. A method of cementing comprising:
   providing a settable composition comprising water and a cementitious component having a determined reactive index; wherein the particle size of the cementitious component has been reduced by way of grinding to adjust the determined reactive index; and
   allowing the settable composition to set to form a hardened mass.

9. A method of cementing comprising:
   providing a settable composition comprising water and a cementitious component having a determined reactive index; wherein the determined reactive index is a measured parameter of the cementitious component divided by the specific surface area of the cementitious component; and
   allowing the settable composition to set to form a hardened mass.

10. The method of claim 9 wherein the measured parameter is compressive strength, Young's modulus, fluid loss, thickening time, a rheological value, free water, or any combination thereof.

11. The method of claim 1 wherein the settable composition comprises a blended cementitious component, the blended cementitious component comprising the cementitious component.

12. The method of claim 11 further comprising estimating performance of the settable composition using the following equation:

$$EP_{blend} = \sum_{i=1}^{n} (RI_i)(SSA_i)(f_i)^m$$

wherein $EP_{blend}$ is an estimated parameter for the blended cementitious component, i is the individual cementitious component from a set of cementitious components 1 to n, n is an integer, $RI_i$ is the reactive index for cementitious component i, $SSA_i$ is the specific surface area for cementitious component i, $f_i$ is the mass fraction of the cementitious component i, and m is a value from 1 to 10.

13. The method of claim 1 further comprising placing the settable composition into a subterranean formation penetrated by a well bore.

14. The method of claim 13 wherein settable composition is used in primary cementing in the well bore.

15. The method of claim 13 wherein the settable composition is used remedial cementing in the well bore.

16. A method of measuring reactivity of a cementitious component comprising:
   measuring a parameter of the cementitious component, the cementitious component having a specific surface area; and
   dividing the measured parameter by the specific surface area of the cementitious component to obtain a reactive index for the cementitious component.

17. The method of claim 16 further comprising preparing a settable composition comprising the cementitious component, and using the reactive index to adjust an amount of the cementitious component in the settable composition.

18. The method of claim 16 wherein the measured parameter is compressive strength, Young's modulus, fluid loss, thickening time, a rheological value, free water, or any combination thereof.

19. The method of claim 9 wherein the cementitious component comprises at least one component selected from the group consisting of Portland cement, calcium aluminate, gypsum, a pozzolanic material, kiln dust, and any combination thereof.

20. The method of claim 9 wherein the settable composition further comprises a second cementitious component, wherein the cementitious component and the second cementitious component have different reactive indexes.

21. The method of claim 20 wherein the cementitious component and the second cementitious component have reactive indexes that vary by a factor of at least about 2:1.

22. The method of claim 20 wherein the cementitious component and the second cementitious component have reactive indexes that vary by a factor of at least about 100:1.

23. The method of claim 9 wherein the settable composition comprises a blended cementitious component, the blended cementitious component comprising the cementitious component.

24. The method of claim 23 further comprising estimating performance of the settable composition using the following equation:

$$EP_{blend} = \sum_{i=1}^{n} (RI_i)(SSA_i)(f_i)^m$$

wherein $EP_{blend}$ is an estimated parameter for the blended cementitious component, i is the individual cementitious component from a set of cementitious components 1 to n, n is an integer, $RI_i$ is the reactive index for cementitious component i, $SSA_i$ is the specific surface area for cementitious component i, $f_i$ is the mass fraction of the cementitious component i, and m is a value from 1 to 10.

* * * * *